United States Patent [19]
Tapper

[11] 4,325,367
[45] Apr. 20, 1982

[54] IONTOPHORETIC TREATMENT APPARATUS

[76] Inventor: Robert Tapper, 1935 Armacost Ave., Los Angeles, Calif. 90025

[21] Appl. No.: 95,632

[22] Filed: Nov. 19, 1979

Related U.S. Application Data

[63] Continuation-in-part of Ser. No. 52,295, Jun. 26, 1979, abandoned, which is a continuation of Ser. No. 806,393, Jun. 13, 1977, Pat. No. 4,164,226.

[51] Int. Cl.³ .................................................. A61N 1/30
[52] U.S. Cl. .............................. 128/207.21; 128/795; 128/803
[58] Field of Search ........... 128/207.21, 783, 791–793, 128/795, 796, 798, 802, 803, 640

[56] References Cited

U.S. PATENT DOCUMENTS

| | | | |
|---|---|---|---|
| 2,590,876 | 4/1952 | Landauer | 128/803 X |
| 2,784,715 | 3/1957 | Kestler | 128/207.21 |
| 3,472,233 | 10/1969 | Sarbacher | 128/783 X |
| 3,991,755 | 11/1976 | Vernon et al. | 128/207.21 |
| 4,082,087 | 4/1978 | Howson | 128/640 |
| 4,092,985 | 6/1978 | Kaufman | 128/802 X |
| 4,141,359 | 2/1979 | Jacobsen et al. | 128/207.21 |
| 4,177,817 | 12/1979 | Bevilacqua | 128/803 X |

FOREIGN PATENT DOCUMENTS 2351670  12/1977  France ........................... 128/207.21

Primary Examiner—Lee S. Cohen
Attorney, Agent, or Firm—Fulwider, Patton, Rieber, Lee & Utecht

[57] ABSTRACT

A self-contained iontophoretic treatment apparatus is provided which includes a support structure on which is mounted a pair of electrodes in generally close proximity to one another as well as a source of electrical power and appropriate controls for delivering electrical power to the electrodes. The electrodes are arranged so that, for example, the palm of a single human hand can be placed on the device and simultaneously contact both electrodes, thereby confining the iontophoretic treatment to the palm surface of the hand. Alternative embodiments of the invention specially adapted for treating the plantar surfaces of the feet and the axillae are also disclosed.

5 Claims, 9 Drawing Figures

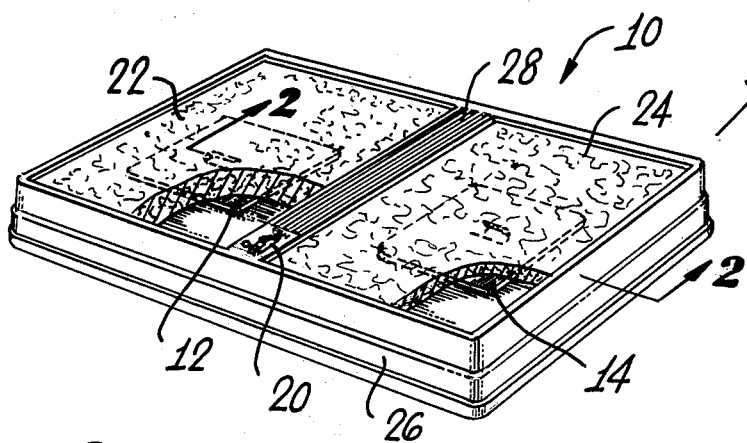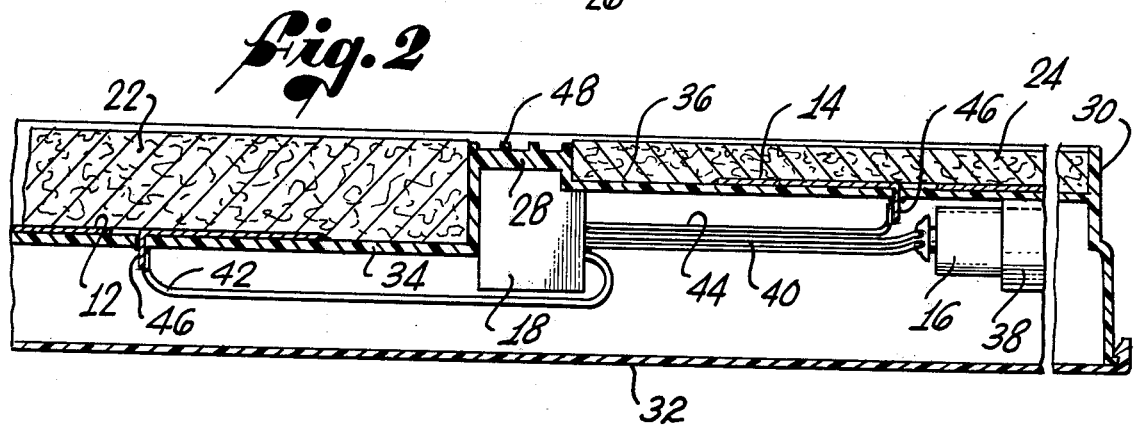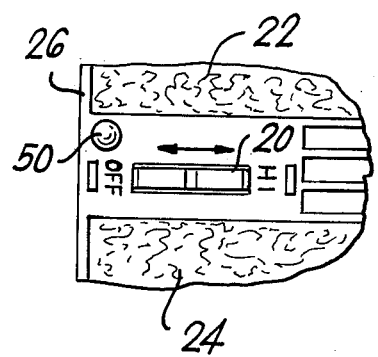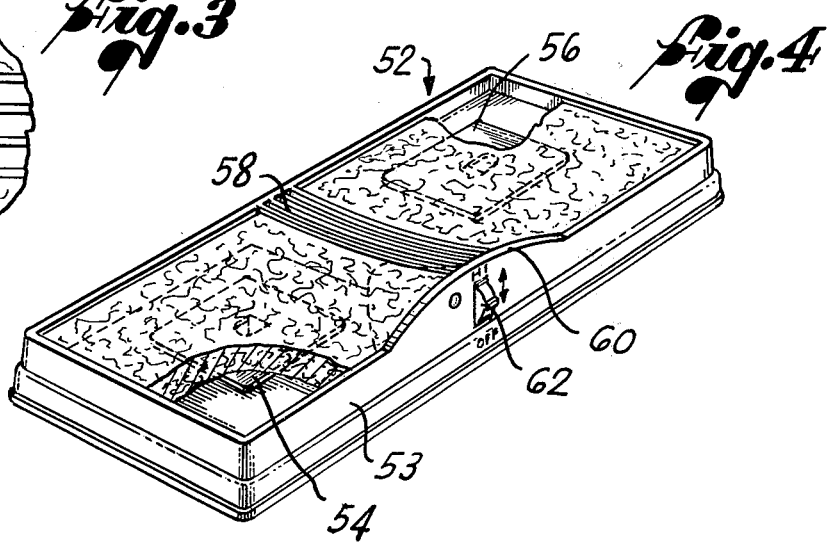

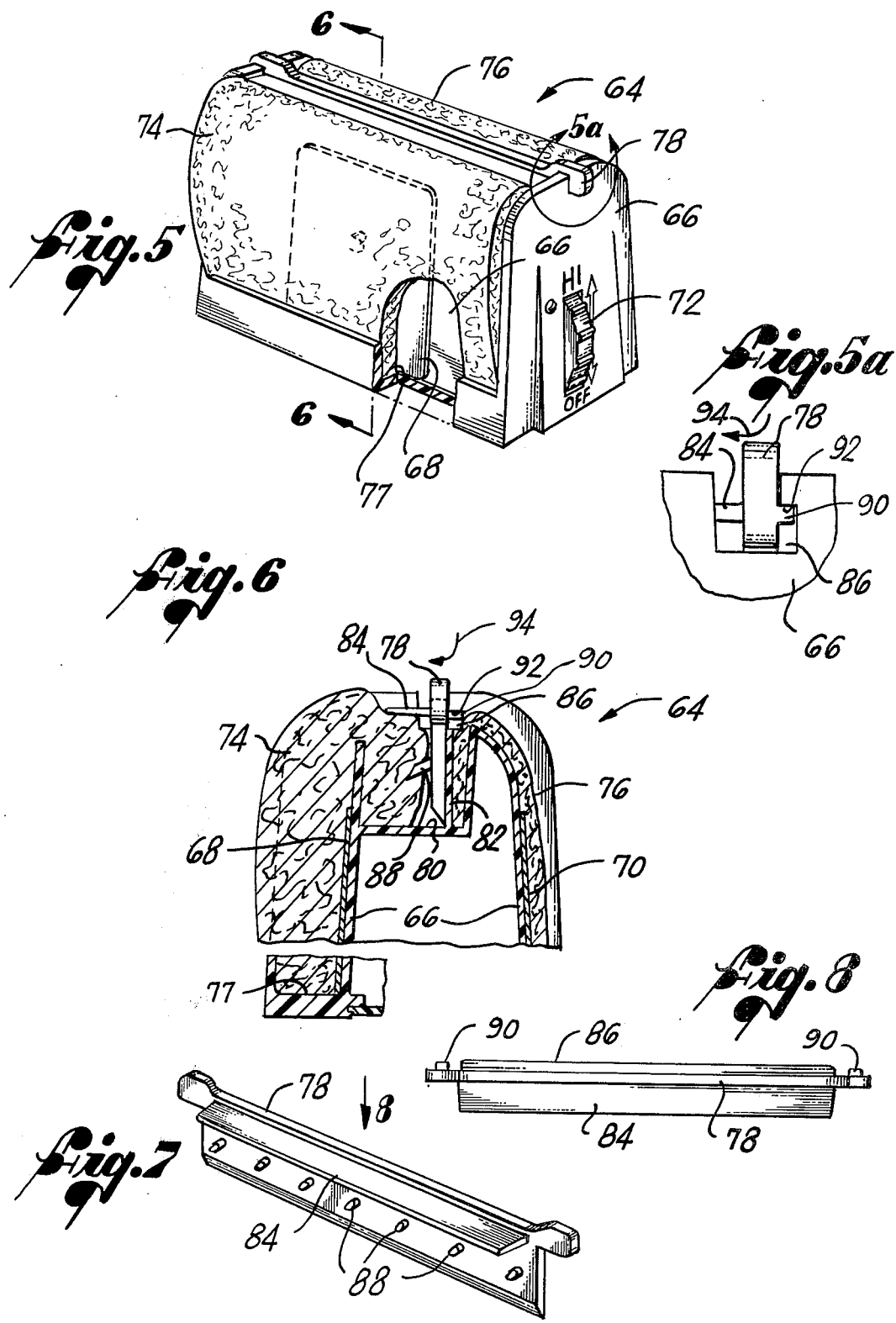

IONTOPHORETIC TREATMENT APPARATUS

BACKGROUND OF THE INVENTION

This is a continuation-in-part of prior application Ser. No. 052,295, filed June 26, 1979, now abandoned which is a continuation of application Ser. No. 806,393, filed June 13, 1977, now U.S. Pat. No. 4,164,226.

This invention relates generally to medical treatment devices, and, more particularly, to a device for conveniently effecting iontophoretic treatment of the surface of the human body.

Iontophoretic treatments have been popular in the past for their polar effects on ionized molecules, causing the ionized molecules to be driven through the skin, usually superficially. This phenomenon has been employed, for example, for the introduction of medicants, or even simply moisture, into the skin of a patient.

In other applications of iontophoretic treatments, some ions of zinc and copper can be employed in the treatment of some skin infections, and chlorine ions have been employed for the loosening of superficial scars. Further, vasodilating drugs can be used in rheumatic and peripheral vascular affections, and skin anesthetic drugs. It has been suggested that application of direct current to carefully selected areas of a living animal can produce anesthetic effects. (See Limoge, *An Introduction to Electroanesthesia*, 1975, University Park Press). In still another application of iontophoretic treatment, it has been suggested that iontophoresis can be employed to effect mass hair removal from the treated area.

F. Levitt in "Archives of Dermatology," Vol. 98 No. 5, November 1968, reports on pps. 505-7 the production of long term anhidrosis by electric treatment of the feet, or hands. However, he disclosed only the use of "a two-inch square of sheet lead" as an electrode. This is "placed in a shallow pan containing enough water to just cover the palm or soles"; there being one electrode and one pan for each palm or sole. His test results indicate that the treatment inhibits perspiration (sweat) where the electric current is provided.

It will be noted that, although this arrangement provides for the desired iontophoretic treatment of the hands or feet, it has the undesirable effect of causing the treatment current to flow through parts of the body not being treated. That is, when this arrangement is being employed for treating a patient's hands, for example, the treatment current flows from one hand to the other through the patient's torso. This can have the undesirable effect of disrupting the normal function of vital body organs or interfering with artificial devices associated with the body, such as an electronic pacemaker, or the like.

From the foregoing, it will be appreciated that it is highly desirable to be able to administer conveniently iontophoretic treatment to a patient, and it is particularly desirable for a person who desires iontophoretic treatment to be able to safely and conveniently administer that treatment to himself. Moreover, it is very desirable to confine the iontophoretic treatment only to the area of the body being treated in order to avoid unnecessarily disrupting the normal function of vital body organs or any artificial devices associated therewith.

As mentioned above, iontophoretic treatment devices known heretofore have been cumbersome and awkward to use, and could only be used by trained medical personnel who had to supervise the administration of the treatment of a patient. These devices frequently included wires leading to electrodes which were difficult to hold in place during the treatment. Moreover, the patient frequently had to be placed in an uncomfortable and inconvenient situation during the treatment, such as holding his hands or feet in pans of water, which further discouraged use of iontophoretic treatment by the medical community. Lastly, iontophoretic treatment devices which employed a pair of electrodes of the same or very similar metals have been subject to corrosion of those electrodes which results in a loss of current over the period of treatment thereby decreasing the effectiveness of the treatment.

Accordingly, there has existed a need for a convenient and effective device for administering iontophoretic treatment to the surface of the human body, which device can be easily and safely used by the person on whom the treatment is being effected, and which device confines the treatment current to the area of the body being treated and which is capable of maintaining the treatment current at a relatively high level throughout a normal treatment period. As will become apparent from the following, the present invention satisfies those needs.

SUMMARY OF THE INVENTION

The present invention resides in a new and improved apparatus for effecting iontophoretic treatment to the surface of a human body, which apparatus can be used safely and conveniently by the person being treated and which may cause the treatment current to flow only through the portion of the body being treated. Moreover, the iontophoretic treatment apparatus of this invention is relatively inexpensive to manufacture, is trouble free and reliable in use, and is capable of sustaining a relatively high level of treatment current over a long period of treatment.

More specifically, the preferred embodiments of this invention are specially adapted for administering iontophoretic treatment to the palm surface of a human hand, the plantar surface of a human foot and the axilla areas of the body. For these purposes, three distinct embodiments are provided.

The first embodiment, which is designed for treating the palm of a hand, is a self-contained, unitary device which includes an upper surface sized to correspond generally to the size of a human hand. Two electrodes are disposed on the upper surface in generally close proximity to one another and are separated by a narrow insulating member. Further, a manual control switch is also located on the upper surface. With this arrangement, a user can simply place his hand palm down on the upper surface of the device, extending across the insulating member and simultaneously contacting both electrodes. By simple manual operation of the switch, as with the thumb, the user can activate the device and thereby easily and conveniently administer iontophoretic treatment to himself.

The second embodiment is specially adapted for administering iontophoretic treatment to the plantar surface of a foot. This embodiment is similar to the first embodiment but is longer and can be narrower to accommodate the shape of a human foot. Further, an arched portion is built into the device along one side and generally at the center thereof. This arched portion assures contact with the arched portion of the plantar surface of a foot. Also, a control switch can be located on the side of the device for easy manual operation.

The third embodiment is substantially different in construction from the first and second embodiments, and is specially adapted for permitting iontophoretic treatment of the axilla portions or armpit areas of the body. To accommodate the contour of the axilla portion of the body, the third embodiment of this invention includes two generally parallel, oppositely facing electrodes mounted on a single unitary support structure. In order to hold this device in place during treatment, the user simply positions the device in his armpit and holds his arm down during the treatment. In this way, the user's hands are free for other activities during the iontophoretic treatment of the axilla area.

In all of the above embodiments, a stainless steel electrode is preferably used for the electrode which is primarily a cathode, and an aluminum electrode is preferably used for the electrode which is primarily an anode. By this arrangement, a minimum of corrosion of the electrodes will occur, and the device will be able to sustain a relatively high operating current over extended periods of time.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view of an iontophoretic treatment device embodying the present invention, and illustrated as arranged for treatment of the palm of a human hand, and having portions thereof broken away to reveal parts not ordinarily visable;

FIG. 2 is an enlarged, fragmentary view, partly in section, of the device illustrated in FIG. 1, and taken substantially along line 2—2 of FIG. 1;

FIG. 3 is a fragmentary top view of a manual control which is provided on the device illustrated in FIG. 1;

FIG. 4 is a perspective view of an alternative embodiment of the iontophoretic treatment device of this invention, illustrated as arranged for treating the plantar surface of a human foot, and shown with certain parts broken away to reveal parts not ordinarily visable;

FIG. 5 is a perspective view of another alternative embodiment of the iontophoretic treatment device of this invention, illustrated as arranged for treating the axilla area of a body, and having a portion broken away to show a detail of the construction thereof;

FIG. 5a is an enlarged view of the portion of the end of the device enclosed within the arrow 5a in FIG. 5;

FIG. 6 is an enlarged, fragmentary view, partly in section, showing an arrangement for retention of electrode pads which can be used with the device illustrated in FIG. 5;

FIG. 7 is a perspective view of the pad retainer shown in FIG. 6; and

FIG. 8 is a top view of the pad retainer, taken generally in the direction of the arrow 8 in FIG. 7.

DETAILED DESCRIPTION

As shown in the exemplary drawings, the present invention is embodied in an iontophoretic treatment apparatus, indicated generally by reference number 10 in FIG. 1, and having a pair of electrodes 12 and 14 for effecting iontophoretic treatment. The apparatus 10 includes a source of electrical power, such as a battery 16 (FIG. 2), which is connected to a suitable control device 18 that in turn is connected to the electrodes 12 and 14.

The control device 18 can include a manual control switch 20 for activating and deactivating the apparatus 10, and if desired, the switch 20 can include a continuous control device, such as a potentiometer, to permit manual control of the level of treatment current administered by the apparatus 10. Further, each of the electrodes 12 and 14 is provided with a moisture absorbing pad 22 and 24 to be interposed between the surface being treated and the electrodes 12 and 14 respectively to ensure adequate electrical contact with the surface to be treated and to distribute that electrical contact over a greater area of the treated surface.

In accordance with the present invention, an iontophoretic treatment device is provided which is self-contained and includes a pair of electrodes 12 and 14 mounted on a single support structure 26 in generally close proximity to one another and separated by a relatively narrow insulating member 28. The support structure 26 also houses the source of electrical power 16 and the control device 18 for controlling the delivery of electrical power to the electrodes. The electrodes 12 and 14 are mounted close enough to one another to permit the surface to be treated, for example, the palm surface of a human hand, to extend across the insulating member 28 and simultaneously contact both electrodes. With this arrangement, a single unitary structure can be employed for administering iontophoretic treatment to a person, and advantageously, the treatment current is confined to the area being treated.

To accomplish this desired result, the support structure 26, in the embodiment illustrated in FIGS. 1 and 2, is generally rectangular, and the electrodes 12 and 14 are mounted on the upper surface of the rectangular structure 26. In this instance, the apparatus 10 is specially adapted for treating the palm surface of a human hand, and accordingly the length and width of the rectangular structure is chosen to correspond generally with the size of a human hand.

More specifically, as can best be seen in FIG. 2, the support structure 26 is comprised primarily of two members, an upper body member 30 and a lower cover 32. The insulating member 28 is formed as part of the body 30 and extends across the middle thereof separating two upwardly facing recesses 34 and 36 in the bottom of which are received the electrodes 12 and 14 respectively. The support structure 26 is preferably constructed of plastic, and the lower cover 32 can simply snap on the body 30 to close the apparatus 10 in order to present a neat appearance and protect the contents of the apparatus.

The source of electrical power, or battery 16, is received in a mounting bracket 38 which is secured to the body 32 in any suitable manner. The pair of electrical leads 40 supply power from the battery to the control device 18 from which power is supplied to the electrodes 12 and 14 through electrical leads 42 and 44, respectively. For the purpose of connecting these leads to the electrodes, a tab 46 is bent downwardly from each electrode and extends through the bottom of the recesses 34 and 36, and the leads 42 and 44 are connected to the downwardly extending tabs 46 in a conventional manner.

As described in greater detail in the above-mentioned patent applications, a porous intervenor or moisture absorbing pad 22 and 24 is interposed between the electrodes 12 and 14 and the surface of the user to be treated. As further described in the above-mentioned patent applications, it is sometimes desirable for one of these pads to be relatively thick while the other need not be thick, and as can be seen from FIG. 2, provision for varying thicknesses in the pads 22 and 24 can easily be made in the apparatus 10 of the present invention by varying the depth of the recesses 34 and 36.

When the pads 22 and 24 are used, it is generally desirable to keep them moist in order to facilitate conduction of electricity through the pads. In order to best retain the moisture within the pads, the recesses 34 and 36 are preferably water-tight and serve as reservoirs for retention of moisture in the pads. To best serve this purpose, the apertures in the bottom of the recesses through which the tabs 46 extend are preferably sealed in any conventional manner after the electrodes have been installed.

To prevent inadvertent short circuiting of the apparatus 10 when in use, the insulating member 28 extends transversely across the apparatus between the recesses 34 and 36 and is of sufficient height to separate the pads 22 and 24. Moreover, in order to ensure that no moisture from the pads can flow across the insulating member 28 and cause a short circuit, the member 28 preferably includes a series of upstanding ribs 48 which also extend transversely across the apparatus 10.

While the pads 22 and 24 can be of any suitable porous material, it has been found that a polyester material is preferred. For example, polyester electrode pads soak up water much more readily than do pads made of wool felt used heretofore, and polyester pads do not exhibit the tendency to shrink which is present in wool pads. Moreover, polyester pads are much more economical to supply, and do not support bacterial life as readily as wool felt pads.

It has also been found that by using the same or similar metals for both electrodes in an iontophoretic treatment device, which has been the common practice heretofore, a substantial loss of current is experienced over the treatment period due to corrosion occurring on one or both of the electrodes. For example, in an iontophoretic treatment device in which both the anode and cathode are aluminum alloy, a significant loss of current is experienced over each treatment period, and each successive treatment period begins at the level of loss experienced at the end of the preceding period. Naturally, after several treatment periods, the iontophoretic treatment device will have lost its effectiveness.

In contrast to this, it has been found that by using a stainless steel electrode as the cathode of the iontophoretic device and an electrode of substantially pure aluminum, such as that available under the commercial designation ALCOA 1100, as the anode, a loss of current of only about six to eight percent occurs over approximately the first one-half hour of treatment, and virtually no losses occur thereafter. Moreover, the device returns to full power at the beginning of each subsequent treatment.

As can best be seen in FIG. 3, the control switch 20 is preferably a continuous control device, such as a potentiometer, to permit the user to adjust the level of iontophoretic treatment being administered. This facilitates the utility of the apparatus 10 for use in the home by the person being treated since it permits the user to select the level of treatment personally desired. Further, a light 50 can be provided adjacent to the switch 20 to indicate whether the apparatus 10 is activated.

An alternative embodiment of the present invention, illustrated as an iontophoretic treatment device 52 in FIG. 4, is specially adapted for treating the plantar surface of a single foot. For this purpose, the configuration of the support structure 53 of this device is generally similar to the configuration of the support structure 26 of the device illustrated in FIGS. 1 and 2. That is, the device is generally rectangular, has a pair of electrodes 54 and 56 disposed on its upper surface and a narrow insulating member 58 separating the electrodes 54 and 56.

To accommodate the shape and contour of the plantar surface of a foot, the foot device 52 is generally longer than the hand device 10, and can be slightly narrower. Further, to assure adequate contact with the entire plantar surface of a foot, particularly with the arch portion of a human foot, a generally arched or raised portion 60 is provided on the upper surface of the device 52, and this arched portion is centrally located on the device along one side thereof.

It is commonly believed that the amount of treatment effected at each electrode is very nearly equal. Accordingly the foot device 52 described herein can be used for treating either the right or left foot by simply reversing the device end-for-end so that the arched portion 60 will cooperate with the arch of either a right or left foot. It will also be noted that a control switch 62 is provided on the side of the device 52 for easy manual operation.

A third embodiment of the present invention, illustrated as an iontophoretic treatment device 64 in FIGS. 5 and 6, is specially adapted for treating the axilla area of a human body. For this purpose, the support structure 66 of the device 64 is not a generally flat rectangular structure as described above, but rather is a generally upright structure having a pair of electrodes 68 and 70. (FIG. 6) in generally parallel planes and facing oppositely from one another. With this arrangement, the iontophoretic treatment device 64 can be positioned in the axilla area and held in place during treatment by the user simply lowering his arm. This arrangement has a significant advantage over prior devices in that the user's hands are relatively free during treatment, making this device particularly convenient to use. Moreover, as in the other devices disclosed herein, the treatment device 64 includes a control switch 72 on the body 66 for manually activating and controlling the level of treatment.

As with the former devices disclosed herein, the iontophoretic treatment device 64 employs porous pads 74 and 76 between the electrodes and the surface being treated, and these pads are preferably to be kept moist to facilitate conductivity. For this purpose, as can best be seen in the cut-away portion of FIG. 5, a water-tight trough 77 is provided along the bottom of the body 66, and the lower end of the pad 74 extends into the trough. This permits the trough 77 to serve as a reservoir for retaining moisture in the pad 74. Naturally, a second trough (not shown) can be provided on the other side of the body 66 to serve as a similar reservoir for the other pad 76.

For the purpose of providing an insulating member between the electrode 68 and 70 and further for holding the pads 74 and 76 in place on the body 66, a pad retainer 78 bears against the upper portion of the pads 74 and 76 and is releasably secured to the body 66, as will be described in greater detail below. As can best be seen in FIG. 6, the upper portion of the body 66 includes a generally U-shaped channel 80 which is divided into two channels by a vertical dividing wall 82. The upper portion of each of the pads 74 and 76 is bent over into one of the two channels, and the dividing wall 82 serves to prevent short circuiting of the device 64 by eliminating any contact between the pads 74 and 76.

To hold the pads 74 and 76 in place, the retainer 78 includes a pair of longitudinally extending flanges 84 and 86 which project laterally a sufficient distance to engage and retain the pads 74 and 76, respectively. In this instance, the flange 84 is arranged to cooperate with the pad 74, and accordingly extends laterally a greater distance than the flange 86. Moreover, if desired, a series of retaining spikes 88 can be provided on the retainer 78 to further assist in holding the thicker pad 74.

In order to releasably secure the retainer 78 to the body 66, the retainer includes a pair of tabs 90 which cooperate with an L-shaped slot 92 in the ends of the body 66, as can best be seen in FIG. 5a. To remove the retainer 78 from the device 64, it is necessary only to press the retainer downwardly and slide it to the left, as indicated by the arrow 54 in FIG. 5a, thereby releasing the tab 90 from the L portion of the slot 92. From this position, the retainer 78 can simply be lifted upwardly out of the channel 80, thereby disengaging it from the pads 74 and 76.

From the foregoing, it will be appreciated that the iontophoretic treatment apparatus of the present invention provides a device which is self-contained and is easy and convenient to use. Moreover, the device of the invention can be fabricated conveniently and economically, is capable of maintaining a relatively high level of operation over an extended period of time, and may advantageously confine the flow of treatment current to the area of the body being treated.

While several particular forms of the invention have been illustrated and described, it will also be apparent that various modifications can be made without departing from the spirit and scope of the invention.

I claim:

1. A self-contained iontophoretic treatment apparatus comprising: a support structure; a source of electrical power and a control means therefor on said support structure; a pair of electrodes mounted on said support structure in generally close proximity to one another, said electrodes being connected to said source of electrical power through said control means; porous pads on said electrodes, and an insulating member extending between said electrodes, a first of said electrodes being connected to said source of electrical power and arranged to act primarily as a cathode, and the other electrode being connected to said source of electrical power and arranged to act primarily as an anode, said first electrode being formed of stainless steel and said other electrode being formed of substantially pure aluminum, said support structure and said electrodes being sized and arranged so that a surface to be treated can extend across said insulating member and simultaneously contact both of said pads, whereby electric current from said electrodes for effecting iontophoretic treatment will pass only through the surface being treated.

2. An iontophoretic treatment apparatus as set forth in claim 1 in which said porous pads are moisture absorbing, said insulating member extending between said moisture absorbing pads.

3. An iontophoretic treatment apparatus as set forth in claim 2 wherein said pads are formed of polyester material.

4. A self-contained iontophoretic treatment apparatus comprising:
a support structure;
a source of electrical power and a control means therefor on said support structure;
a pair of electrodes mounted on a treatment surface of said support structure in generally close proximity to one another, said electrodes being connected to said source of electrical power through said control means;
porous pads on said electrodes, and an insulating member extending between said electrodes on said treatment surface, said treatment surface being the upper surface of said support structure and being sized to conform generally with the size of the plantar surface of a human foot, said treatment surface including a centrally located raised portion along one side thereof to cooperate with the arch portion of said plantar surface of said foot, said insulating member being disposed transversely across said treatment surface between said electrodes so that said plantar surface of said foot to be treated can be placed on said treatment surface extending across said insulating member and simultaneously contact both of said pads, whereby electric current from said electrodes for effecting iontophoretic treatment will pass only through said plantar surface of said foot being treated.

5. A self-contained iontophoretic treatment apparatus comprising:
a support structure;
a source of electrical power and a control means therefor on said support structure;
a pair of electrodes mounted on a treatment surface of said support structure in generally close proximity to one another, said electrodes being connected to said source of electric power through said control means;
porous pads on said electrodes, and an insulating member extending between said electrodes on said treatment surface, said support structure forming a generally upright housing, said treatment surface including two generally vertical, parallel planes on said housing facing oppositely from one another and the top of said upright housing connecting said oppositely facing planes, said treatment surface being sized to conform generally with the size of a human axilla, said insulating member being disposed transversely across said treatment surface at the top of said upright housing and between said electrodes so that a human axilla to be treated can extend across said insulating member and simultaneously contact both of said pads, whereby electric current from said electrodes for effecting iontophoretic treatment will pass only through the surface of the axilla being treated.

* * * * *